Figure 1:
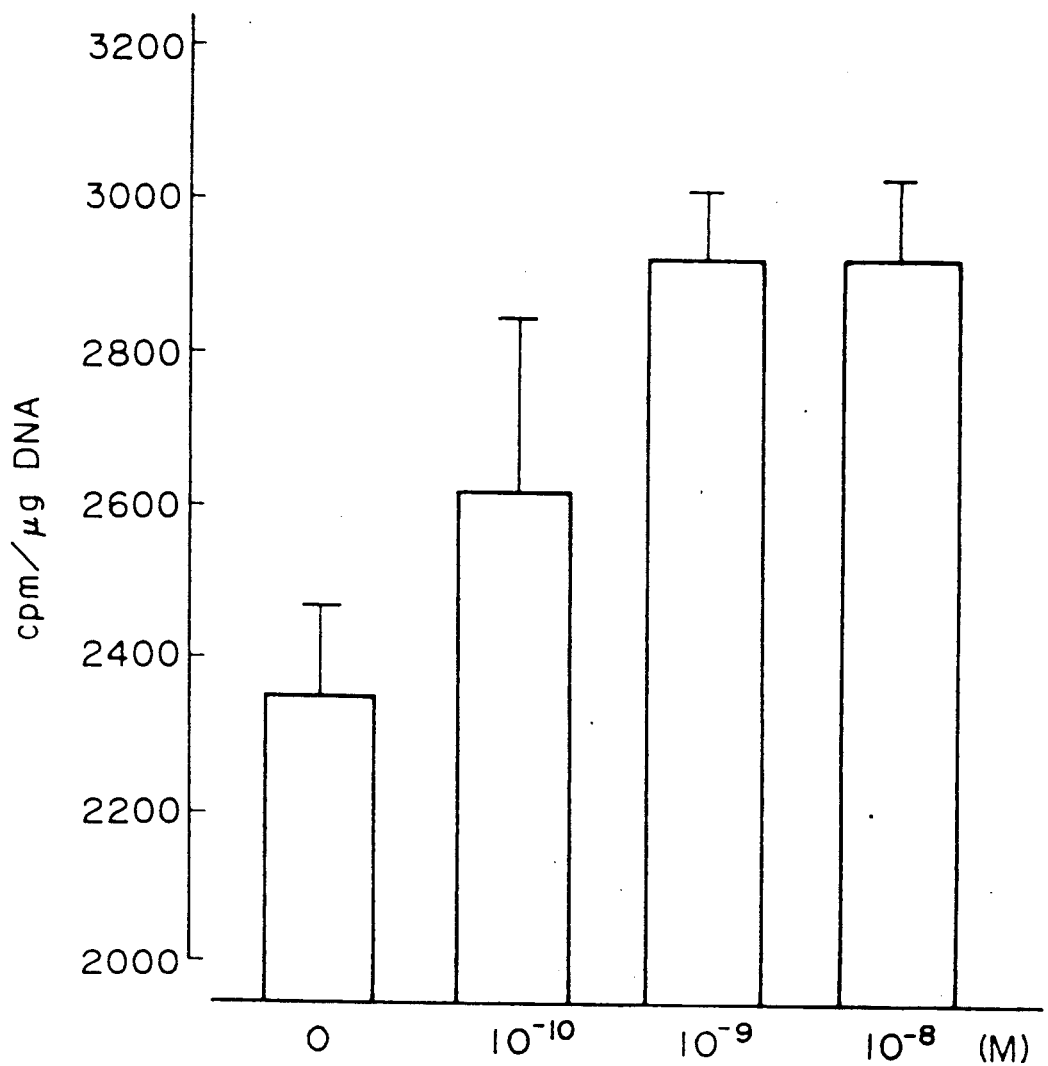

United States Patent [19]

Matsumoto et al.

[11] Patent Number: 5,053,401
[45] Date of Patent: Oct. 1, 1991

[54] OSTEOGENESIS PROMOTION WITH USE OF VITAMIN D DERIVATIVES

[75] Inventors: Toshio Matsumoto; Yasuho Nishii, both of Tokyo, Japan

[73] Assignee: Chugai Seiyaku Kabushiki Kaisha, Tokyo, Japan

[21] Appl. No.: 485,702

[22] Filed: Feb. 27, 1990

[30] Foreign Application Priority Data

Feb. 28, 1989 [JP] Japan .................................. 1-48098

[51] Int. Cl.$^5$ ............................................. A61K 31/59
[52] U.S. Cl. ................................................... 514/167
[58] Field of Search ........................................ 514/167

[56]    References Cited
U.S. PATENT DOCUMENTS 4,891,364 1/1990 Kubodera et al. .................. 514/167

OTHER PUBLICATIONS

Holick et al., C.A. 82:110660r (1975).
Kubodera et al., C.A. 106:84945e (1987).
Abe et al., C.A. 108:88191v (1988).
Abe et al., C.A. 110:69959b (1989).
Valaja et al., C.A. 113:109898b (1990).

Primary Examiner—Shep K. Rose
Attorney, Agent, or Firm—Browdy and Neimark

[57]    ABSTRACT

An osteogenesis promotion with use of a vitamin D derivative of the formula:

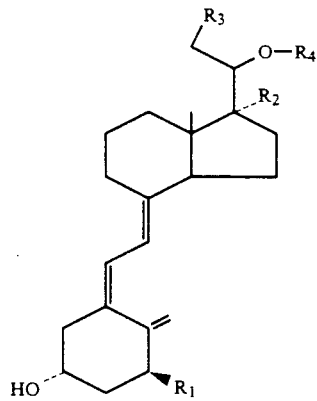

wherein $R_1$, $R_2$ and $R_3$, which may be the same or different, each represents a hydrogen atom or a hydroxyl group; and $R_4$ is a hydrogen atom or a lower alkyl group having 4-6 carbon atoms that may or may not be substituted by a hydroxyl group, are disclosed. A pharmaceutical composition comprising the above derivatives is useful as a therapeutic agent for osteoporosis.

3 Claims, 1 Drawing Sheet

OSTEOGENESIS PROMOTION WITH USE OF VITAMIN D DERIVATIVES

This invention relates to osteogenesis promotion with use of a vitamin D derivative of the formula:

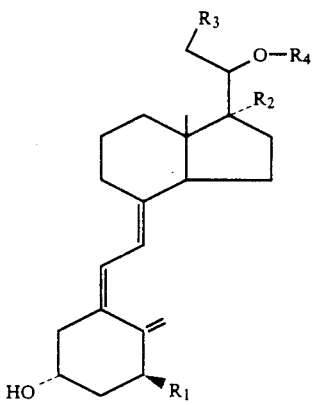

wherein $R_1$, $R_2$ and $R_3$, which may be the same or different, each represents a hydrogen atom or a hydroxyl group; and $R_4$ is a hydrogen atom or a lower alkyl group having 4-6 carbon atoms that may or may not be substituted by a hydroxyl group.

A number of physiological actions of vitamin D derivatives have been discovered recently and one of the major roles played by Vitamin D derivatives is their activity as calcium regulating hormones. It is now well known that vitamin D derivatives such as $1\alpha,25$-dihydroxyvitamin $D_3$ promotes calcium absorption through the small intestine, re-absorption of calcium by the kidney, as well as dissolution of bone-calcium and osteogenesis. However, $1\alpha,25$-dihydroxyvitamin $D_3$ has the serious drawback that it can cause hypercalcemia upon prolonged and continuous administration and hence this compound is not completely satisfactory for use as an osteogenesis promoting agent.

Upon these circumstances, the present inventor conducted intensive studies in order to develop an osteogenesis promoting agent that can be administered for prolonged and continuous period without causing any side effects. As a result, the inventor found that the compound specified herein is capable of promoting osteogenesis in spite of its inability to promote calcium absorption through the small intestine. This fact was established in an experiment with a clone MC3T3-E1 cells established from new bone mouse calvaria. This compound of the present invention also proved to be effective in suppressing the decrease in bone-salt in an experiment conducted with osteoporotic model rats.

The present invention has been accomplished on the basis of further studies on these new observations.

The drawing is a histogram showing the effectiveness of the compound of the present invention in promoting the $^{45}$Ca uptake by MC3T3-E1 cells.

The compound used as the active ingredient for promoting osteogenesis is already described in Japanese Patent Public Disclosure No. 61-267550 and is known to have an immunoregulating action and the ability to induce differentiation in tumor cells. However, no information is given in this patent that suggests the osteogenesis promoting action of the compound.

The compound of the present invention can be synthesized by the procedure described in U.S. Pat. No. 4,891,364. It has an osteogenesis promoting action and is useful as a therapeutic agent for osteoporosis.

The compound of the present invention is formulated in a suitable dosage form, such as one for oral administration or injection, in the usual manner. A preferred dosage form is a capsule or tablet.

The dose of the compound of the present invention differs slightly with the severity of the disease and the method of administration. Unlike the prior art vitamin D derivatives, this compound will not cause hypercalcemia and hence can be administered in a fairly high dose. The preferred range of dose is from 0.01 to 10 $\mu$g daily per human adult.

EXPERIMENT 1

Using a clone MC3T3-E1 established from new bone mouse calvaria, the effectiveness of $1\alpha,3\beta$-dihydroxy-$20\alpha$-(3-hydroxy-3-methylbuthyloxy)-9,10-seco-5,7,10(19)-pregnatriene in causing calcification by promoting the cellular uptake of $^{45}$Ca was investigated in accordance with the procedure of Sudo et al. [J. Cell Biol., 96, 191 (1983)]. The results are shown in the accompanying drawing, in which the vertical axis plots the $^{45}$Ca uptake per DNA and the horizontal axis plots the concentration of the compound of the present invention added.

EXPERIMENT 2

(a) Preparation of Osteoporotic Model Rats

Ten-month old F344/Du female rats (purchased from Japan Charles River Co., Ltd.) were acclimated by feeding on an ordinary diet for 1 week. The rats were then subjected to OVX (ovariectomy) under anesthetization with ether. In 2 weeks, the wound healed almost completely and the rats were thereafter fed on a 0.5% Ca diet. A sham operation group was prepared as a control and fed on a normal 1.16% Ca diet. The point of time when the feed was shifted to the 0.5% Ca diet was assigned "zero months". Ion-exchanged water was used to avoid contamination by Ca impurity, and the rats were kept in separate cages, individually and not in groups, for 3 months to insure uniformity in the growth of animals. In order to make sure that each animal would have the same intake of vitamin $D_3$ which would cause substantial effects on bone metabolism, they were fed a vitamin D-free diet and administered orally 150 IU/body of vitamin $D_3$ on a once-a-week basis.

(b) Administration of the Compound of the Present Invention

After 4 months of feeding on 0.5% Ca diet, $1\alpha,3\beta$-dihydroxy-$20\alpha$-(3-hydroxy-3-methylbuthyloxy)-9,10-seco-5,7,10(19)-pregnatriene was dissolved in an amount of 1.0 $\mu$g/kg in MCT (middle-chain aliphatic acid triglyceride) and the solution was administered orally to the rats for 2 months on a three-times-a-week basis. The control group was administered MCT alone. Each group consisted of 5-10 animals.

(c) Bone-salt Measurement

Twenty-four hours after the last administration of the compound of the present invention, blood was totally withdrawn from the rats under anesthetization with ether. The right femoral bone was taken from each animal and fixed with 70% ethanol after removing the muscle and other tissues. After the ethanol fixation, the amounts of bone-salt in the proximal point, diaphysis and distal point of the femoral bone of each individual were measured with Dichroma Scan DCS-600 (ALOKA, Inc.)

The above results shown that the decrease in the amount of bone-salt in each site of measurement was significantly suppressed in the group administered 1.0 μg/kg of the compound of the present invention.

What is claimed is:

1. A method for promoting osteogenesis without causing hypercalcemia, comprising: administering to a person in need of osteogenesis an amount effective to promote osteogenesis without causing hypercalcemia of 1α,3β-dihydroxy-20α-(3-hydroxy-3-methylbuthyloxy)-9,10-seco-5,7,10(19)-pregnatriene.

2. A method according to claim 1 wherein the person suffers from osteoporosis.

3. A method according to claim 1 wherein said effective amount is about 0.01 μg to about 10 μg daily.

* * * * *